United States Patent [19]

Edhag

[11] Patent Number: 5,010,894
[45] Date of Patent: Apr. 30, 1991

[54] INTRAVASCULAR ELECTRODE LEAD USABLE FOR CARDIAC DEFIBRILLATION

[76] Inventor: Knut O. Edhag, Sandstensvägen 11, Bromma, Sweden, S-161 39

[21] Appl. No.: 399,489
[22] PCT Filed: Jan. 9, 1989
[86] PCT No.: PCT/SE89/00002
  § 371 Date: Sep. 7, 1989
  § 102(e) Date: Sep. 7, 1989
[87] PCT Pub. No.: WO89/06148
  PCT Pub. Date: Jul. 13, 1989

[30] Foreign Application Priority Data

Jan. 7, 1988 [SE] Sweden ............................. 00019/88

[51] Int. Cl.⁵ ............................................... A61N 1/05
[52] U.S. Cl. ...................................... 128/785; 128/786
[58] Field of Search .............................. 128/784–786, 128/419 P, 419 D

[56] References Cited

U.S. PATENT DOCUMENTS

| | | | |
|---|---|---|---|
| 3,865,118 | 2/1975 | Bures | 128/419 P X |
| 3,866,615 | 2/1975 | Hawson | 128/784 X |
| 4,154,247 | 5/1979 | O'Neill | 128/419 P |
| 4,289,138 | 9/1981 | Halvorsen | 128/786 |
| 4,402,328 | 9/1983 | Doring . | |
| 4,641,656 | 2/1987 | Smits . | |
| 4,660,571 | 4/1971 | Hess et al. . | |

FOREIGN PATENT DOCUMENTS

| | | | |
|---|---|---|---|
| 0009732 | 4/1980 | European Pat. Off. | 128/785 |
| 3300050 | 7/1984 | Fed. Rep. of Germany | 128/785 |
| 2310775 | 12/1976 | France | 128/786 |
| 435339 | 9/1984 | Sweden . | |

OTHER PUBLICATIONS

Berens et al., "New Stable ... Loop", A. J. Cardiology, vol. 34, Sep. 1974, pp. 325–332.

Primary Examiner—Lee S. Cohen
Attorney, Agent, or Firm—Fleit, Jacobson, Cohn, Price, Holman & Stern

[57] ABSTRACT

An intravascular electrode lead usable for cardiac defibrillation comprises a lead body (11) and an electrode arrangement (12) carried by said lead body and insertable into an atrial or ventricular room, said electrode arrangement comprising a number of elongate flexible electrodes (13). The electrodes (13) are anchored to the lead body (11) adjacent to each other at their one ends. For the rest, they are resiliently movable in relation to the lead body (11) from laterally retracted positions, in which they are located adjacent to each other, to laterally expanded positions, in which they may bear resiliently against the surrounding wall (22) of said room.

4 Claims, 2 Drawing Sheets

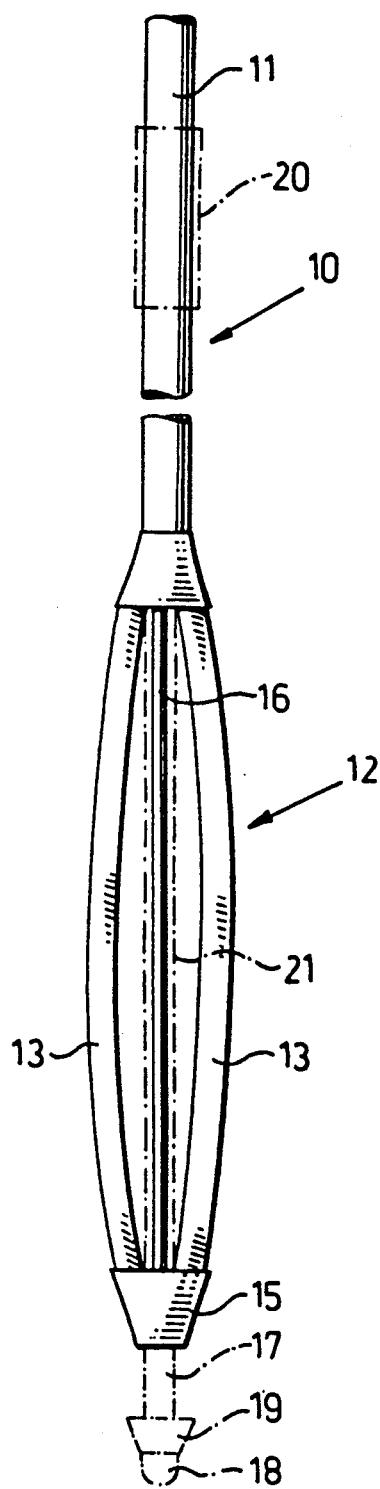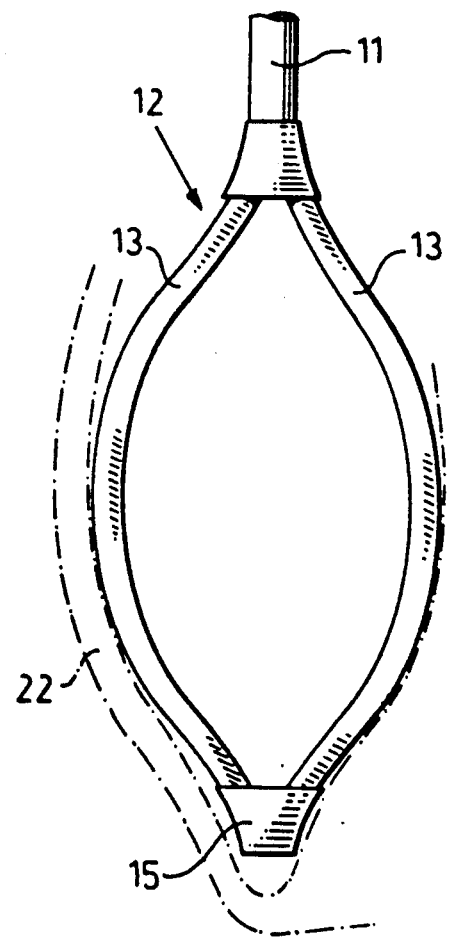

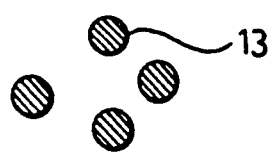
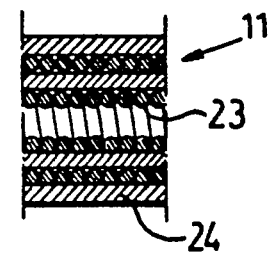
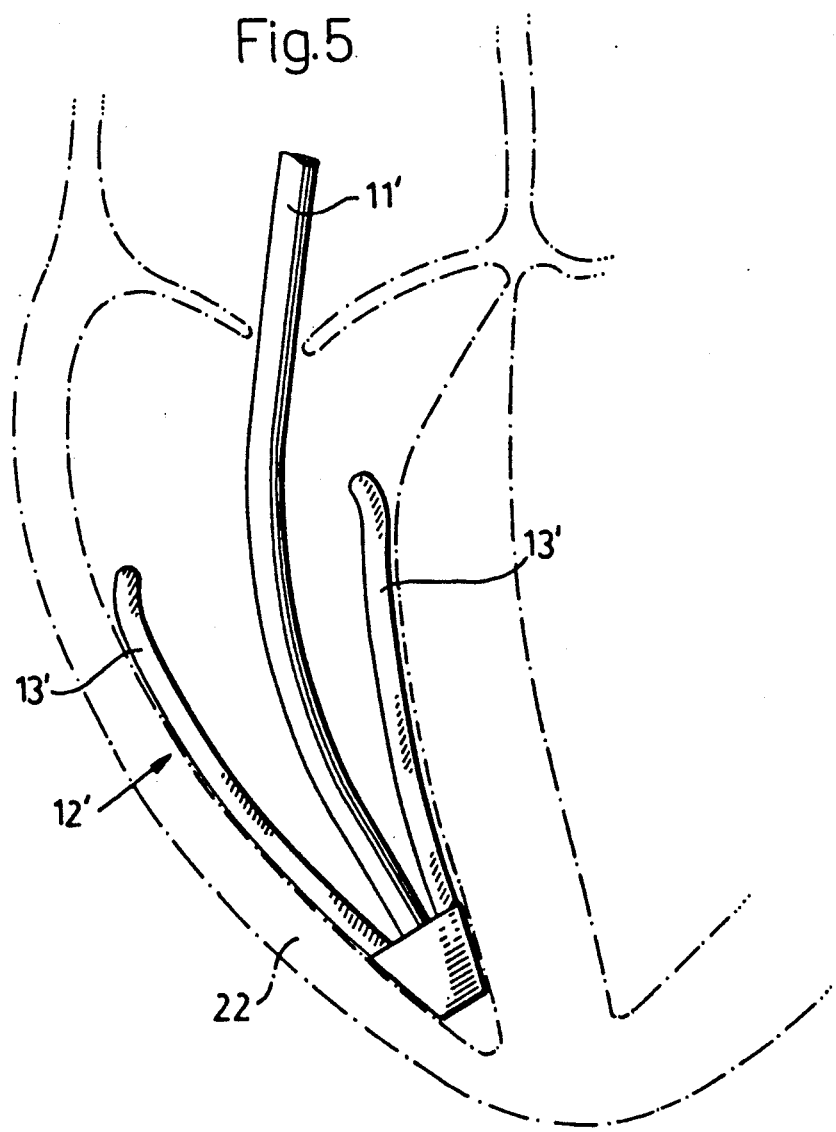

INTRAVASCULAR ELECTRODE LEAD USABLE FOR CARDIAC DEFIBRILLATION

FIELD OF THE INVENTION

The present invention relates to an intravascular electrode lead usable for cardiac defibrillation, said lead being of the kind comprising an elongate electrically insulated lead body, and an electrode arrangement carried by said lead body and insertable into an atrial or ventricular cardiac room, said electrode arrangement comprising a number of elongate flexible electrodes which are arranged to be brought into resilient contact with circumferentially spaced portions of the surrounding wall of said room.

BACKGROUND OF THE INVENTION

An electrode lead of said kind is previously known through U.S. Pat. No. 4,641,656 which discloses an electrode lead having an electrode arrangement which is insertable into a ventricle and which has two elongate defibrillating electrodes which are connected to each other by means of a bent connecting portion. Each one of said two defibrillation electrodes is formed by an electrically conductive wire wound on a portion of the lead body. This construction of the electrode arrangement has several drawbacks. Firstly, as a consequence of the fact that the lead body is utilized as a supporting core for the electrodes, the electrodes will have a comparatively high stiffness which is unfavourable in several respects. Secondly, due to the special shape of the electrode arrangement, it is difficult to place said arrangement in the desired position in the ventricle without running the risk of causing damages on the surrounding tissue. Furthermore, in practice, it is not possible to chose the number of defibrillation electrodes in the electrode arrangement larger than two. Finally, the electrode arrangement can only be placed in a ventricle, while it is not suited to be placed in an atrium as the bent connecting portion could then damage and disturb the cardiac valves.

SUMMARY OF THE INVENTION

The invention has for its purpose to provide an improved electrode lead of the kind initially specified which eliminates the above drawbacks of the known lead above described.

According to the invention, for the above purpose, there is proposed an electrode lead primarily characterized in that said electrode arrangement comprises two or more elongate flexible electrodes which are anchored to the lead body adjacent to each other at their one ends, while, for the rest, they are movable in relation to the lead body in such a manner as to be able to move under the action of spring forces from laterally retracted positions, in which they extend close to each other along their whole length and in which they permit an unobstructed insertion of the electrode arrangement into said room, to laterally expanded positions, in which they may bear resiliently against the surrounding wall of said room.

The above construction of the electrode arrangement of the electrode lead allows the elongate flexible electrodes to be made considerable less stiff than what is possible in the above described known lead. Moreover, the electrode arrangement may be inserted in the desired position in an atrial or ventricular room without difficulty and without running the risk of causing any damage on the surrounding tissue. Additionally, the number of elongate flexible electrodes in the electrode arrangement may be chosen substantially larger than two. Thus, the electrode arrangement may for instance include between four and eight such electrodes.

A special advantage, following from the possibility of increasing the number of electrodes in the electrode arrangement offered through the invention, is that the total contact area between the elongate electrodes and the surrounding wall of the cardiac room in which the electrode arrangement is placed may be considerably increased in an easy manner. This means that one may permit the current pulses supplied by means of said electrodes to have a high amplitude without having to run the risk of causing the current density in the tissue provided in contact with the electrodes to become high enough to cause serious damage on said tissue. In this connection, it could be mentioned that the required energy contents of the defibrillation pulses usually amount to several ten joules.

The electrode lead, proposed according to the invention, is well suited for use in combination with one or more epicardial defibrillation electrodes as well as for intracardial defibrillation.

According to a preferred embodiment of the invention, at their other ends, the elongate flexible electrodes included in said electrode arrangement may be anchored adjacent to each other to a common interconnecting member which is arranged for limited movement in the longitudinal direction of the electrode arrangement. Said interconnecting member may advantageously be arranged, during the insertion of the electrode arrangement into said room, to be releasably held in a position in which, in its turn, it may hold the electrodes in their laterally retracted positions, and from which it may be moved under the action of spring forces in a direction towards said one ends of the electrodes upon an insertion of the electrode arrangement into said room and a release of said arrangement, in order hereby to permit a lateral expansion of the electrodes along their inner portions. For releasably holding the interconnecting member in said position during the insertion of the electrode arrangement, one may use for instance a stylet wire insertable through a longitudinal central cavity in the lead body.

The required spring force for causing said movement of the interconnecting member and said lateral expansion of the electrodes may be generated by the electrodes themselves through the action of a spring-bias stored in each electrode. In order to avoid the need for storing any higher spring-bias in the electrodes and instead making it possible to make the electrodes highly flexible to enable them to adapt themselves easily to the shape of the surrounding tissue which varies continuously during the operation of the heart, said spring force or at least a substantial portion thereof may however suitably be generated by means of an extension of the lead body formed as an elastic tensible member connected to said interconnecting member.

According to an alternative embodiment of the invention, the electrodes may be freely movable in lateral directions in relation to each other at their other ends. The electrodes may then suitably have a higher stiffness against bending in the circumferential direction of the electrode arrangement than in the transversal direction of said arrangement. Furthermore, the electrode lead may comprise means for releasably holding the free ends of the electrodes in positions close to each other in order hereby to facilitate an insertion of the electrode arrangement into said atrial or ventricular room and any possible removal of said arrangement from said room. By way of example, one possible means usable for said purpose is a catheter adapted to be pushed over the lead body and the electrode arrangement.

All electrodes of the electrode arrangement may be electrically connected to each other. Such a construction of the electrode arrangement makes it possible to have all electrodes connected to a common electrical conductor embedded in the lead body.

However, as an alternative, one or more electrodes of the electrode arrangement may be electrically insulated from the remaining electrodes of said arrangement. However, this will necessitate a corresponding increase in the number of conductors placed in the lead body.

Below the invention will be further described with reference to the accompanying diagrammatic drawings, in which;

BRIEF DESCRIPTION OF THE DRAWINGS

FIG. 1 shows a side elevation of an intravascular electrode lead according to a first embodiment of the invention, selected by way of example, illustrating an electrode arrangement of said lead, formed by a number of elongate flexible side by side electrodes, in a state in which it may be unobstructedly inserted into an atrial or ventricular room;

FIG. 2 shows a partial side elevation of the electrode lead according to FIG. 1, illustrating said electrode arrangement in a state in which its electrodes are arranged to bear resiliently against the surrounding wall of said room;

FIG. 3 shows a diagrammatic cross-sectional view of an electrode arrangement comprising four electrodes;

FIG. 4 is a fragmentary view showing a portion of the lead body in longitudinal section; and FIG. 5 is a partial side elevation, corresponding to FIG. 2, of an electrode lead according to a second embodiment of the invention.

DESCRIPTION OF THE INVENTION

The electrode lead 10 shown in FIG. 1 comprises an elongate electrically insulated lead body 11, at its one end carrying an electrode arrangement, generally designated 12, which is intended to be inserted into an atrial or ventricular cardiac room. Said electrode arrangement consists of a number of elongate resiliently flexible electrodes 13 which extend in mutually overlapping conditions along the length of electrode arrangement 12 and which is located in spaced apart positions along the circumference of said arrangement. For the sake of clearness, in FIG. 1, only two diametrically opposite electrodes 13 have been shown. However, the number of such electrodes may be chosen substantially larger. For instance, arrangement 12 may comprise between four and eight electrodes 13 which may be uniformly or non-uniformly distributed along the circumference of said arrangement. In FIG. 3, there is shown a diagrammatic cross-sectional view of an electrode arrangement comprising four non-uniformly distributed electrodes 13.

At their upper ends according to FIG. 1, electrodes 13 are mechanically anchored to lead body 11 and connected to one or more electrical conductors embedded in said body but not shown in said Figure. By means of said conductors, the electrodes are connected to a corresponding number of terminals 14 provided at the other end of the lead for connecting the electrodes to outer electric circuits. At their lower ends, electrodes 13 are anchored adjacent to each other to a common interconnecting member 15.

In FIG. 1, electrodes 13 have been shown in laterally retracted positions, in which they are located at a very short distance from each other along their whole length and in which they permit an unobstructed insertion of electrode arrangement 12 into an atrial or ventricular room. In FIG. 1, the spacing between electrodes 13 has been shown exaggerated. Thus, the real spacing may be substantially shorter than shown in said Figure. In order to make it possible to hold electrodes 13 in their laterally retracted positions during the insertion of electrode arrangement 12, lead 10 is provided with a stylet wire 16 which extends through a central longitudinal cavity in body 11 and by means of which interconnecting member 15 may be releasably held in the position shown in FIG. 1, in which it is located at maximum distance from body 11.

When electrode arrangement 12 has been inserted into the room in question, stylet wire 16 may be removed. Due to a spring-bias stored in each electrode 13, the electrodes may then move from their laterally retracted positions, shown in FIG. 1, to their laterally expanded positions, shown in FIG. 2, in which they may bear resiliently against the surrounding wall of said room, at least along a substantial portion of their length. In FIG. 2, the cardiac tissue 22 forming said wall has been indicated in dash-dotted lines. If the electrodes are highly flexible, the required spring force for moving the electrodes to their positions shown in FIG. 2 may alternatively, at least to a large extent, be generated by means of an extension 21 of the lead body indicated in dash-dotted lines in FIG. 1 and formed as an elastic tensible member which extends to interconnecting member 15 and is connected to the latter.

As indicated in dash-dotted lines in FIG. 1, in addition to electrodes 13, contained in arrangement 12, electrode lead 10 may have a number of additional electrode means. Thus, the electrode lead may for instance be provided with a tip electrode 18 carried by an additional extension 17 projecting from interconnecting member 15. If electrode arrangement 12 is placed in the right ventricle, said tip electrode may be brought into contact with the apex. Extension 17 may also be provided with suitable anchor means 19, as diagrammatically indicated. Moreover, electrode lead 10 may also be provided with an electrode 20 located above electrode arrangement 12 and mounted externally on body 11. This electrode may be positioned so as to cause it to become located within the superior vena cava when electrode arrangement 12 is inserted into the right ventricle. Naturally, electrodes 18 and 20 must also be connected to suitable terminals, similar to terminals 14, by means of which they may be connected to outer electric circuits.

FIG. 4 illustrates how, in a manner known per se, lead body 11 may be built up from a number of concentric layers, comprising flexible conductors 23, formed by helically wound metal wire, and flexible tubes 24, consisting of an electrically insulating material and surrounding said conductors. If the inner conductor 23 is connected to apex electrode 18, the elastic tensible member 21 may be formed by said conductor and the adjacent surrounding flexible tube 24 which for instance may consist of silicon rubber.

The embodiment shown in FIG. 5 differs from the embodiment according to FIGS. 1 and 2 in that the electrodes 13' included in electrode arrangement 12' are freely movable in relation to each other at their one ends. This construction of the electrode arrangement 12' results in that electrodes 13' may more easily be brought into contact with the surrounding cardiac tissue 22, indicated in dash-dotted lines, along almost their entire length. Furthermore, electrodes 13' are anchored to body 11' at their lower ends instead of at their upper ends.

In order to reduce the risk of any unintentional contact between electrodes 13' as a result of a deflection of said electrodes in the circumferential direction of electrode arrangement 12', said electrodes may suitably be formed so as to have a higher stiffness against bending in the circumferential direction of the electrode arrangement than in the transversal direction of said arrangement. Such an increased stiffness against bending in the circumferential direction may for instance be achieved by forming the electrodes as generally band-like members. By shaping the electrodes in such a manner it is also possible to increase their contact area with the surrounding cardiac tissue.

In the embodiment according to FIG. 5, the electrode lead may also be provided for instance with a catheter or any other means by which electrodes 13' may be held in positions close to each other in order to facilitate an insertion of electrode arrangement 12' into the intended cardiac room.

In both embodiments, electrodes 13 or 13', respectively, may preferably be formed by a core of an electrically insulating material and a conductive covering provided on said core and consisting for instance of a metal wire wound around said core. The electrodes may also consist entirely of partially of a memory metal having a suitably selected transition temperature in order to ensure that a spring-bias stored within the electrodes will become released only when the electrodes have been inserted into the intended cardiac room. Alternatively, the electrodes may be built up on a core of a memory plastic material.

Electrodes 13 or 13', respectively, should have as large a length as possible in order hereby to form large electrode surfaces. Preferably, the electrode length should be at least about 20-30 millimeters. However, even a larger electrode length may be des per se. The outer diameter or transverse dimension of the electrodes may for instance be in the order of about 2 millimeters. If the electrode arrangement 12 or 12' contains four electrodes, the above dimensions of the electrodes will result in that the total electrode area of the electrode arrangement will amount to about 5-about 7 square centimeters.

The invention is not restricted to the embodiments above described and shown in the drawings. Instead, many alternative embodiments are feasible within the scope of the invention. By way of example, it could be mentioned that, especially in case the elongate flexible electrodes contained in the electrode arrangement are freely movable in relation to each other at their one ends, it is possible to use electrodes of mutually different length and to bias the electrodes into mutually different shapes. Further, it is also possible to provide an electrode lead with two electrode arrangements of the kind above described at two different locations along the length of said lead, in which case the two electrode arrangements may be located in such positions relatively to each other as to make it possible to have one of them placed in an atrium and the other in the corresponding ventricle.

I claim:

1. An intravascular electrode lead usable for cardiac defibrillation, said lead comprising an elongate electrically insulated lead body having a central longitudinal cavity and an electrode arrangement carried by said lead body and extending substantially in the longitudinal direction of the lead body from an end thereof and insertable into an atrial or ventricular cardiac room, said electrode arrangement comprising at least two elongate resiliently flexible electrodes which are arranged to be brought into resilient contact with circumferentially spaced portions of the surrounding wall of said room, said electrodes extending in longitudinally mutually overlapping and circumferentially spaced apart relationship from a first end of said electrode arrangement, where said electrodes are anchored to the lead body adjacent to each other and to a second end of said electrode arrangement where said electrodes are anchored adjacent to each other to a common interconnecting member, which is arranged to each other to a common interconnecting member, which is arranged for limited movement in the longitudinal direction of the electrode arrangement to permit the electrodes to move in relation to each other under the action of spring forces from laterally retracted positions in which they extend close to each other along their whole length and in which they permit an unobstructed insertion of the electrode arrangement into said room, to laterally expanded positions, in which they may bear resiliently against the surrounding wall of said room, the electrode lead further comprising a stylet wire removably inserted through the central longitudinal cavity in the lead body and applied against said interconnecting member to releasably hold the interconnecting member in a position in which said member, in its turn, may hold said electrodes in their laterally retracted positions, and an elastic tensile member, forming an extension of the lead body and extending to the interconnecting member and connected thereto to apply a spring-force on the interconnecting member, tending to assist in moving said electrodes to their said laterally expanded positions.

2. An intravascular electrode lead usable for cardiac defibrillation, said lead comprising an elongate electrically insulated lead body having a central longitudinal cavity and an electrode arrangement carried by said lead body and extending substantially in the longitudinal direction of the lead body from an end thereof and insertable into an atrial or ventricular cardiac room, said electrode arrangement comprising at least two elongate resiliently flexible electrodes which are arranged to be brought into resilient contact with circumferentially spaced portions of the surrounding wall of said room, said electrodes extending in longitudinally mutually overlapping and circumferentially spaced apart relationship from a first end of said electrode arrangement, where said electrodes are anchored to the lead body adjacent to each other, and to a second end of said electrode arrangement, where said electrodes are anchored adjacent to each other to a common interconnecting member, which is arranged for limited movement in the longitudinal direction of the electrode arrangement to permit the electrodes to move in relation to each other under the action of spring forces from laterally retracted positions in which they extend close to each other along their whole length and in which they permit an unobstructed insertion of the electrode arrangement into said room, to laterally expanded positions, in which they may bear resiliently against the surrounding wall of said room, the electrode lead further comprising a stylet wire removably inserted through the central longitudinal cavity in the lead body and applied against said interconnecting member to releasably hold the interconnecting member in a position in which said member, in its turn, may hold said electrodes in their laterally retracted positions, and an elastic tensile member, forming an extension of the lead body and extending to the interconnecting member and connected thereto to apply a spring-force on the interconnecting member, tending to assist in moving said electrodes to their said laterally expanded positions, and a top electrode connected to the lead body through said elastic tensile member and an additional extension coupled between said tip electrode and said interconnecting member, said additional extension being provided with anchor means for anchoring said electrode lead.

3. An intravascular electrode lead usable for cardiac defibrillation, said lead comprising an elongate electrically insulated lead body having a central longitudinal cavity and an electrode arrangement carried by said lead body and extending substantially in the longitudinal direction of the lead body from an end thereof and insertable into an atrial or ventricular cardiac room, said electrode arrangement comprising at least two elongate resiliently flexible electrodes which are arranged to be brought into resilient contact with circumferentially spaced portions of the surrounding wall of said room, all electrodes of said electrode arrangement being electrically connected to each other and extending in longitudinally mutually overlapping and circumferentially spaced apart relationship from a first end of said electrode arrangement, where said electrodes are anchored to the lead body adjacent to each other and to a second end of said electrode arrangement, where said electrodes are anchored adjacent to each other to a common interconnecting member, which is arranged for limited movement in the longitudinal direction of the electrode arrangement to permit the electrodes to move in relation to each other under the action of spring forces from laterally retracted positions in which they extend close to each along their whole length and in which they permit an unobstructed insertion of the electrode arrangement into said room, to laterally expanded positions, in which they may bear resiliently against the surrounding wall of said room, the electrode lead further comprising a stylet wire removably inserted through the central longitudinal cavity in the lead body and applied against said interconnecting member to releasably hold the interconnecting member in a position in which said member, in its turn, may hold said electrodes in their laterally retracted positions, and an elastic tensile member, forming an extension of the lead body and extending to the interconnecting member and connected thereto to apply a spring-force on the interconnecting member, tending to assist in moving said electrodes to their said laterally expanded positions.

4. An intravascular electrode lead usable for cardiac defibrillation, said lead comprising an elongate electrically insulated lead body having a central longitudinal cavity and an electrode arrangement carried by said lead body and extending substantially in the longitudinal direction of the lead body from an end thereof and insertable into an atrial or ventricular cardiac room, said electrode arrangement comprising at least two elongate resiliently flexible electrodes which are arranged to be brought into resilient contact with circumferentially spaced portions of the surrounding wall of said room, at least one electrode of said electrode arrangement being electrically insulated from the remaining electrodes of said arrangement, all said electrodes extending in longitudinally mutually overlapping and circumferentially spaced apart relationship from a first end of said electrode arrangement, where said electrodes are anchored to the lead body adjacent to each other and to a second end of said electrode arrangement, where said electrodes are anchored adjacent to each other to a common interconnecting member, which is arranged for limited movement in the longitudinal direction of the electrode arrangement to permit the electrodes to move in relation to each other under the action of spring forces from laterally retracted position in which they extend close to each other along their whole length and in which they permit an unobstructed insertion of the electrode arrangement into said room, to laterally expanded positions, in which they may bear resiliently against the surrounding wall of said room, the electrode lead further comprising a stylet wire inserted through the central longitudinal cavity in the lead body and applied against said interconnecting member to releasably hold the interconnecting member in a position in which said member, in its turn, may hold said electrodes in their laterally retracted positions, and an elastic tensile member, forming an extension of the lead body and extending to the interconnecting member and connected thereto to apply a spring-force on the interconnecting member, tending to assist in moving said electrodes to their said laterally expanded positions.

* * * * *

UNITED STATES PATENT AND TRADEMARK OFFICE
CERTIFICATE OF CORRECTION

PATENT NO. : 5,010,894

DATED : April 30, 1991

INVENTOR(S) : Knut O. EDHAG

It is certified that error appears in the above-identified patent and that said Letters Patent is hereby corrected as shown below:

Col. 6, lines 23-24, delete "which is arranged to each other to a common interconnecting member"

Col. 7, line 16, delete "top " and insert --tip--

Col. 8, line 40, after "wire" insert --removably--.

Signed and Sealed this

Twenty-seventh Day of October, 1992

Attest:

DOUGLAS B. COMER

Attesting Officer     Acting Commissioner of Patents and Trademarks